(12) United States Patent
Walters

(10) Patent No.: US 9,404,797 B2
(45) Date of Patent: Aug. 2, 2016

(54) PLASMONIC SPECTROSCOPIC SENSOR AND CUVETTE THEREFOR

(71) Applicant: Integrated Plasmonics Corporation, San Francisco, CA (US)

(72) Inventor: Robert Joseph Walters, San Francisco, CA (US)

(73) Assignee: INTEGRATED PLASMONICS CORPORATION, San Francisco, CA (US)

( * ) Notice: Subject to any disclaimer, the term of this patent is extended or adjusted under 35 U.S.C. 154(b) by 0 days.

(21) Appl. No.: 14/648,843

(22) PCT Filed: Dec. 3, 2013

(86) PCT No.: PCT/US2013/072927
§ 371 (c)(1),
(2) Date: Jun. 1, 2015

(87) PCT Pub. No.: WO2014/089120
PCT Pub. Date: Jun. 12, 2014

(65) Prior Publication Data
US 2015/0308893 A1     Oct. 29, 2015

Related U.S. Application Data

(60) Provisional application No. 61/784,345, filed on Mar. 14, 2013, provisional application No. 61/734,934, filed on Dec. 7, 2012.

(51) Int. Cl.
    *G01N 21/25*     (2006.01)
    *G01J 3/02*     (2006.01)
    (Continued)

(52) U.S. Cl.
CPC ............. *G01J 3/0229* (2013.01); *G01J 3/0208* (2013.01); *G01J 3/42* (2013.01); *G01N 21/64* (2013.01); *G02B 5/008* (2013.01)

(58) Field of Classification Search
CPC ....... G01J 3/02; G01N 21/253; G01N 21/251; G01N 21/255; G01N 21/27; G01N 21/314
USPC .................................................. 356/300–445
See application file for complete search history.

(56) References Cited

U.S. PATENT DOCUMENTS

| 4,516,857 A | 5/1985 | Preston et al. |
| 4,659,222 A | 4/1987 | Ekholm |

(Continued)

FOREIGN PATENT DOCUMENTS

| EP | 1 217 426 A1 | 6/2002 |
| WO | 98/34098 A1 | 8/1998 |

(Continued)

OTHER PUBLICATIONS

International Search Report (ISR) issued in PCT/US2013/072927 mailed in Apr. 2014.

(Continued)

*Primary Examiner* — Abdullahi Nur
(74) *Attorney, Agent, or Firm* — Chen Yoshimura LLP

(57) ABSTRACT

A spectroscopic measurement system, which may utilize multiple plasmonic filters associated with a cuvette to monitor different wavelengths of light. The spectroscopic measurement system may measure absorbance and or fluorescence, and may have built-in low cost CMOS image sensor(s). Reagents and samples may be introduced to the cuvette from a fluidics manifold. Multiple sets of combined cuvettes, image sensors and plasmonic filters may utilize a single fluidics manifold for reagent and sample distribution.

11 Claims, 12 Drawing Sheets

(51) Int. Cl.
*G01J 3/42* (2006.01)
*G02B 5/00* (2006.01)
*G01N 21/64* (2006.01)

(56) References Cited

U.S. PATENT DOCUMENTS

| | | | |
|---|---|---|---|
| 5,116,759 | A | 5/1992 | Klainer et al. |
| 5,442,169 | A * | 8/1995 | Kunz ............... G01D 5/26 250/227.18 |
| 5,644,512 | A | 7/1997 | Chernoff et al. |
| 5,674,457 | A | 10/1997 | Williamsson et al. |
| D433,150 | S | 10/2000 | Wahlqvist et al. |
| 6,838,650 | B1 | 1/2005 | Toh |
| 7,466,409 | B2 | 12/2008 | Scherer et al. |
| 8,076,128 | B2 | 12/2011 | Liederman et al. |
| 8,231,268 | B2 | 7/2012 | Krol et al. |
| 8,284,401 | B2 | 10/2012 | Choi et al. |
| 2002/0039184 | A1 * | 4/2002 | Sandusky ............ G01J 3/02 356/369 |
| 2005/0114332 | A1 | 5/2005 | Lee et al. |
| 2006/0034729 | A1 | 2/2006 | Poponin |
| 2007/0070347 | A1 | 3/2007 | Scherer et al. |
| 2008/0135739 | A1 | 6/2008 | Kim et al. |
| 2010/0039648 | A1 | 2/2010 | Garcia da Fonseca |
| 2010/0046060 | A1 | 2/2010 | Lee et al. |
| 2010/0157306 | A1 | 6/2010 | Choi et al. |
| 2011/0085167 | A1 | 4/2011 | Guan et al. |
| 2011/0111487 | A1 | 5/2011 | Goh et al. |
| 2012/0225475 | A1 | 9/2012 | Wagner et al. |
| 2014/0176939 | A1 | 6/2014 | Shah |

FOREIGN PATENT DOCUMENTS

| | | |
|---|---|---|
| WO | 2006/009724 A2 | 1/2006 |
| WO | 2011/106057 A2 | 9/2011 |
| WO | 2012/054351 A2 | 4/2012 |
| WO | 2014/123613 A1 | 8/2014 |
| WO | 2014/143234 A1 | 9/2014 |
| WO | 2014/143235 A1 | 9/2014 |
| WO | 2014/158248 A1 | 10/2014 |

OTHER PUBLICATIONS

Written Opinion (PCT/ISA/237) issued in PCT/US2013/072927 mailed in Apr. 2014.
Huang et al., "Micro-hole drilling with femtosecond fiber laser", SPIE Paper No. 8607-19, Photonics West 2013, Feb. 2-7, 2013.
International Search Report (ISR) issued in PCT/US2013/072929 mailed in Apr. 2014.
Written Opinion (PCT/ISA/237) issued in PCT/US2013/072929 mailed in Apr. 2014.
International Search Report (ISR) issued in PCT/US2013/07290 mailed in Apr. 2014.
Written Opinion (PCT/ISA/237) issued in PCT/US2013/072930 mailed in Apr. 2014.
International Search Report (ISR) issued in PCT/US2013/072932 mailed in Apr. 2014.
Written Opinion (PCT/ISA/237) issued in PCT/US2013/072932 mailed in Apr. 2014.
International Search Report (ISR) issued in PCT/US2013/072936 mailed Apr. 2014.
Written Opinion (PCT/ISA/237) issued in PCT/US2013/072936 mailed in Apr. 2014.
Fiedler, "Incoherent Broad-Band Cavity-Enhanced Absorption Spectroscopy", 2005, Berlin.
Oliva-Chatelain et al., "Basics of UV-Visible Spectroscopy", Physical Methods in Chemistry and Nano Science, Jun. 5, 2010.
Chen et al., "A CMOS Image Sensor Integrated with Plasmonic Colour Filters", Plasmonics, Dec. 2012, vol. 7, Issue 4, (abstract) Springer Link.
Mansuripur et al., "Plasmonic nano-structures for optical data storage", Optics Express, Aug. 3, 2009, vol. 17, No. 16, pp. 14001-14014.
Genet et al., "Light in tiny holes", nature, Jan. 4, 2007, vol. 445, pp. 39-46.
Koerkamp et al., "Strong Influence of Hole Shape on Extraordinary Transmission through Periodic Arrays of Subwavelength Holes", Physical Review Letters, May 7, 2004, vol. 92, No. 18, pp. 183901-1-183901-4.
Jones et al., "Surface Plasmon assisted extraordinary transmission in metallic nanohole arrays and its suitability as a bio-sensor", Journal of Physics: Conference Series 307, IOP Publishing, 2011, pp. 1-7.
Tok et al., "Unidirectional broadband radiation of honeycomb plasmon antenna array with broken symmetry", Optics Express, Nov. 7, 2011, vol. 19, No. 23, pp. 22731-22742.
Pacifici et al., "Universal optical transmission features in periodic and quasiperiodic hole arrays", Optics Express, Jun. 9, 2008, vol. 16, No. 12, pp. 9222-9238.
Singh et al., "Surface Plasmon Resonance Enhanced Transmission of Light through Gold-Coated Diffraction Gratings", Analytical Chemistry, May 15, 2008, vol. 80, No. 10, pp. 3803-3810.
U.S. Appl. No. 14/095,971, filed Dec. 3, 2013.
U.S. Appl. No. 14/766,551, filed Aug. 7, 2015.
U.S. Appl. No. 14/774,990, filed Sep. 11, 2015.
U.S. Appl. No. 14/775,266, filed Sep. 11, 2015.
U.S. Appl. No. 14/775,299, filed Sep. 11, 2015.

* cited by examiner

PLASMONIC SPECTROSCOPIC SENSOR AND CUVETTE THEREFOR

TECHNICAL FIELD

The present disclosure relates to the field of spectroscopy, including spectroscopic instrumentation and methods for enabling biological and chemical sensors capable of detecting biological or chemical substances, in part by the use of low cost, optical integrated specimen handling cuvettes and structures.

BACKGROUND

Spectrometers measure properties of light over a portion of the electromagnetic spectrum. Spectrometers usually employ a source of electromagnetic energy, and various optical devices such as mirrors and gratings as optical filters for dispersing the light to the detector, as well as a detector to detect the light intensity as a function of wavelength. Existing devices for detecting the light properties include electronic photodetectors such as photodiode arrays, charge-coupled devices (CCD) or CMOS active pixel sensor arrays.

Optical spectrometers are used to detect and quantify the characteristics or concentration of a physical, chemical or biological target object. Medical diagnostic machines using optical spectrometers allow for characterization of chemical and biological information that can be used to detect disease, track associated health markers, or identify dangerous fluid borne chemicals, using only small amounts of blood, urine, saliva, or other physical specimen. However, widespread adoption of this technology has been limited in part due to the cost and size of spectrometer equipment. Typically, only laboratories with complex testing protocols and highly skilled technicians could perform accurate spectroscopic analysis. The time required to deliver samples to the lab, along with the cost of shipping and tracking to prevent misidentification has prevented wider use of spectroscopic diagnostics, and limited the type of testing that is available.

One of the factors limiting widespread adoption of diagnostic spectrometers is the high cost of the associated specimen handling structures and filters suitable for spectroscopic analysis. Attempts have been made to provide spectrometers using low cost cuvettes that can be easily cleaned or cheaply disposed of after single use. For example, U.S. Pat. No. 8,231,268, titled "Screening system and method for analyzing a plurality of biosensors" and assigned to Corning Inc. discloses a cuvette containing system that can analyze using a grating sensor, a reflectometric interference spectroscopy (RIFS) sensor, or a surface plasmon resonance (SPR) sensor. Cuvettes useful with the system include both cuvette strips/bars and rotor cuvette systems. For example, the rotor cuvette system can be employed in combination with a 1-channel liquid handling arrangement mounted directly on a rotary axis to make it very easy to position with respect to devices for liquid handling or measurement. The typical rotor cuvette system is an injection molded article which is made from the same plastic materials as those commonly used to make microplates. Rotor cuvette system can support flow through cuvettes where each cuvette can contain a grating biosensor, an optical transducer structure, or micro-optical interferometers. This rotor cuvette system can also be optimized for measurements of absorbance, fluorescence or luminescence, and widely available from manufacturers such as Hitachi and Olympus.

Cleanable cuvettes and flow chambers for various spectroscopic applications have also been disclosed. For example, U.S. Pat. No. 5,116,759 assigned FiberChem Inc., discloses reservoir sensors for detecting and quantifying inorganic species such as cations, anions and non-ionic species; organic species and pharmaceutical products; and biological species such a viruses, bacteria, antigens and enzymes. The system encompasses a wide range of light interaction techniques and a large number of sensing chemistries. The design allows for the sensing agent to be removed, the cell cleaned and new sensing material added automatically without contamination of sample or surrounding area. Different replaceable reservoir cells can be easily inserted and removed from the sensor body. In one disclosed embodiment, a miniaturized modular reservoir sensor is produced which is easy and inexpensive to manufacture, rugged, reliable, easy to use, and reproducibly uniform. The sensor is small, typically having dimensions of length (optical path-source to detector) of 0.25" to 1.0", a reservoir diameter (inside) of 0.125" to 0.5", and a volume of 10-200 microliters. The cell body can be made of thermoplastic polymer impervious to water. A preferred light source is a high luminosity, high directivity light emitting diode (LED), with 30-40 microwatts of power.

DETAILED DESCRIPTION

Figure 1:
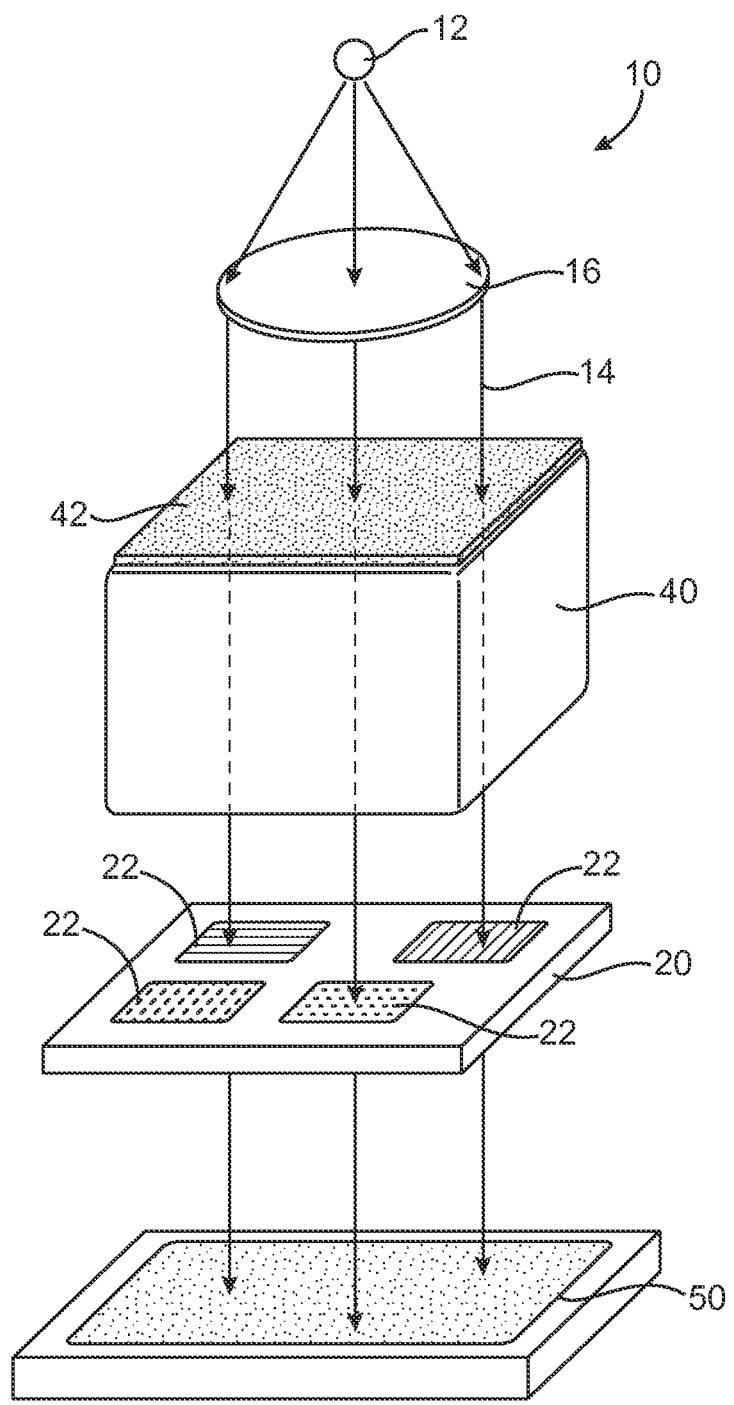
FIG. 1 is a cartoon illustrating a spectrometer system containing a light source directed into a sample containing cuvette, with light passing through the cuvette being filtered by plasmonic filters and light intensity measured by a detector.

A suite of novel structures and methods is provided to enable superior and cost effective spectrometric applications. A collimating element directs light from the light source to provide a collimated light beam, which in turn may be directed through a fixed or removable cuvette. The cuvette may be arranged to have a first and second opposed, parallel, flat and at least partially mirrored surfaces, or may alternatively be configured such that the two opposed sides may each have a slight wedge angle, typically much less than one degree. One partially mirrored surface can include a structured color filter such as a plasmonic filter, which differentially transmits selected wavelengths of light. FIG. 1 illustrates a spectrometer system containing a light source directed into a sample containing cuvette, where light passing through the cuvette may interact with plasmonic filters and the transmitted light intensity may be measured by a detector. As seen in FIG. 1, a compact and low cost spectrometer system 10 incorporating surface plasmon filter set 20 is illustrated. The surface plasmon filter set supports one or more patches 22, with each patch acting to filter light based on various properties, including wavelength or polarization angles. As will be appreciated, each patch may include a number of plasmonic structures in an array, in which case, the patch is referred to as a plasmonic patch or plasmonic filter in this disclosure.

In spectrometer system 10, light source 12 emits light 14 that is collimated by collimator 16, with light 14 directed to pass through cuvette 40. Cuvette 40 has at least one partially mirrored side 42. Cuvette 40 may contain one or more internal chambers capable of holding fluid samples. In this embodiment, the combination of mirrored side 42 and partially reflective plasmonic filter set 20 causes some percentage of light to be reflected back through cuvette 40, increasing the effective path length of light passing through the fluid. Light that passes through cuvette 40 may be modified by surface plasmon filter set 20, with each patch 22 selectively eliminating, enhancing, or otherwise modifying wavelength or intensity of selected light wavelengths during transmission. Patterned and filtered light may be detected by one or more addressed pixels on sensor 50, with the pixels associated with a portion of a transmission pattern and light intensity from that portion being measured. Such measured changes in light intensity can be used to monitor the presence, absence, or absolute or relative concentration of analyte(s), or a change in concentration due to diffusion, flow, or kinetics of a reaction of analyte(s) diffusing into, held, bound, in or associated with the cuvette.

As used herein, any reference to an "optical wave," "electromagnetic wave," "light wave," or "light" will be understood to include the other terms, except as specifically indicated otherwise. The light source 12 can include monochromatic, multiple wavelengths, single bandpass, broadband, or polychromatic light. The light can be circularly polarized, linearly polarized, elliptically polarized, non-polarized, or selectively polarizable, wherein the polarization angle and or phase of linearly polarized light may be adjusted. The light source 12 can also include light emitting diodes ("LEDs"), organic light emitting diodes (OLEDs), quantum dot light emitting diodes (QLEDs), carbon nanotube LEDs, lasers, tunable lasers, vertical cavity surface emitting lasers (VCSELs), filament lamps, discharge lamps, sunlight, or super luminescent diodes. Other light can include UV, visible, IR, coherent, semi-coherent, incoherent, light selectively filtered by bandpass, multipass, longpass, or shortpass filters, or multiple filters in combination. In certain embodiments, sunlight can be direct natural sunlight, filtered, screened, diffused or reflected sunlight. Combinations of the foregoing light sources can be used, including multiple light sources of the same type (e.g. ganged LEDs to increase intensity), combinations of differing light sources intended to extend the range of wavelengths (e.g. IR LEDs combined with optical lasers), or provide intensity enhancement to selected wavelengths (e.g. such as may be provided by a broadband light source with selected high intensity, narrow bandwidth LEDs). As will be appreciated, the temporal or temperature stability of wavelength range, resolution, intensity or other aspects of the light can vary according to the application and available internal or external calibration.

Collimating element 16 can include a spherical lens, an aspheric lens, graded index (GRIN) lenses, light wave guides, mirrors or combinations thereof. Other collimating elements are possible, and in certain embodiments that receive substantially collimated light from the light source, a discrete collimating element may not be required. In operation, collimating element 16 generates a collimated beam of light 14. The focal length of collimating element 16 may be selected based on the properties of the optical wave emitted by light source 12 to achieve the required incident light beam 14. Typically, a divergence or convergence angle of less than 1.0 degrees may be desired, but depending on the application and constraints of the optical system, larger divergence or convergence angles can be tolerated as needed for the desired effective finesse and transmission of the cuvette. In some embodiments, a beam splitter or several beam splitters may be utilized to separate different input light wavelengths, which may thence be utilized in different areas or regions of the plasmonic filter set. In a further embodiment, a grating or prism with slits may be utilized, with optional band pass or high or low pass filters to select different input light wavelengths which may be utilized in different areas or regions of the plasmonic filter set. In a further embodiment, the grating or prism may be manually or automatically adjustable, and a manually or automatically adjustable slit may be provided such that a wavelength and bandpass may be manually or automatically adjusted. In some embodiments, selected wavelengths and band passes may be utilized as part of an automated protocol. In yet further embodiments, a continuous scan over a range of wavelengths may be automatically performed, permitting the generation of a continuous data set of absorption as correlated with time.

Optionally, collimated light can be passed through an optical pattern generator to convert input light into output light having a preselected spatial layout and intensity pattern. This pattern may be created using diffraction, refraction, reflection, and/or other mechanisms, or a combination thereof. The optical pattern generator can include diffractive optical elements containing a glass, plastic, and/or fused silica chip designed and patterned by holography, photolithography, interference lithography, nanoimprint lithography, scribing, molding, and/or other methods to create a predefined illumination pattern from incident light. The optical pattern generator also may employ non-diffractive optics. For example, the generator could employ a lens array that focuses a large collimated beam. Alternatively, or in addition, refractive or reflective optical elements, such as a lens or beam splitter, can be used. The collimated beam from the collimator can be expanded and directed into a lenslet array that would focus the separated light onto multiple sample sites. A combination of refractive and diffractive optical elements may be utilized, for example, utilizing lenslets to focus light to different cuvettes or to different patches within a cuvette, while a diffractive optical element or a set of diffractive optical elements associated directly with each cuvette or patch may generate a more localized illumination pattern associated with each cuvette or patch, generating spots associated with patches and/or plasmonic filters. The localized illumination pattern may be closely aligned with said patches or plasmonic filters. In a further embodiment, multiple diffractive elements may be utilized wherein one diffractive element may be utilized to produce spots of uniform intensity associated with each cuvette or patch, and a second diffractive element or set of diffractive elements may be utilized to produce spots of light associated with each patch or plasmonic filter.

The optical pattern generator may be also used to generate any desired pattern of light, including one-dimensional or two-dimensional patterns (or arrays) and periodic or aperiodic patterns. For example, a diffractive chip or similar optical pattern generator may be used to create any regularly shaped beam. For example, in applications requiring multiple cuvettes, the pattern may be an array of substantially equally spaced substantially equally intense spots positioned to correspond to the spacing of the cuvettes. Alternatively, the arrays could be positioned so that only specific regions within the same cuvette are addressed, or an array of light spots may be configured and positioned so that a number of specific regions may be illuminated on several cuvettes. The spacings and diameter of the spots may be uniform on all cuvettes and within all cuvettes, or may vary between different cuvettes, and within a single cuvette, or may vary both between and within cuvettes. In some embodiments, the spacings of plasmonic filters within a single patch may be uniform, but may vary from patch to patch.

In some embodiments, wherein different cuvettes or different sections of a cuvette may have plasmonic filters associated with detectors which have different sensitivities and or different dynamic ranges, the intensity of the different spots may be adjusted to correspond with the different sensitivities and or dynamic ranges.

In some embodiments, uniform illumination across individual samples rather than across the entire illumination pattern may be desired, particularly with very large area arrays. However, uniform illumination across the entire pattern may be unnecessary for many assays, particularly assays such as kinetic and cellular assays that involve reading the samples before start of the kinetic or cellular assay, since the pre-start measurement may act as a reference for the post-start measurement.

As shown in FIG. 1, cuvette 40 can be made of glass or transparent plastic material. A cuvette can be designed for single use analysis and disposal of a sample, or can be designed to allow multiple uses. Multiple internal cuvette chambers may be preferred when both control(s) and samples need to be compared. As will be appreciated, cuvette designs supporting multiple use applications can provide for washing and sterilization, or alternatively, can involve multiple single use chambers individually disposed in the cuvette, with separate sample or control fill inputs. In certain embodiments, the cuvette 40 can be separately filled outside the spectrometer system, and later inserted into the spectrometer system for analysis, while in other embodiments one or more input and output ports can be integrally formed to allow fill or flushing of the cuvette while it is in an analysis position within the spectrometer system. The cuvette can have a single or multiple flow channels, typically consisting of an input channel(s) and an output channel(s), along with suitable valving or fluid control mechanisms.

The cuvette functions both as a fluid reservoir and an optical cavity. Without excluding other geometries, the cuvette chamber will typically be cylindrical or conical in shape, and have a top surface capable of facing a light source and a bottom surface facing an image sensor(s). The top side of the cuvette facing the light source is generally transparent so as to admit incident light. In certain embodiments, the cuvette can be partially or completely coated or attached to light filters or absorbers to reduce or enhance transparency at some or all wavelengths. In some embodiments, at least one of the internal face of the top side of the cuvette (contacting or near the cuvette cavity) and the exterior face of the top side of the cuvette (not contacting, and away from the cuvette cavity) is at least partially reflective to incident light and therefore forms one facet of an optical cavity. This facet will typically be coated with a thin film optical coating to engineer a desired optical response. Other coatings or inserts into the cuvette can be used to isolate chambers or redirect light, including opaque walls or sidewalls that reduce optical crosstalk, light absorbing or reflecting coatings, or the like. In effect, using cuvette supported (or adjacently positioned) films or structures forms a partially mirrored optical cavity permitting light to travel multiple times between top and bottom of cuvette, effectively increasing the sample path length, wavelength dependent absorption, interaction with plasmonic filter set and improved probability of interacting with related detector(s).

In some embodiments, selected sections of a cuvette may be utilized as control sections. In some embodiments, control sections may not have any target molecules or may be associated with reference samples of known composition and effect, and thus may be utilized to normalize variations in the output of the light source, absorbance of the fluid under observation, temperature, pressure of the input fluid, variations in the size, reflectivity and optical transmission of a consumable at different wavelengths. In other embodiments, one or more reference samples of known composition and effect and or calibration standards may be provided, either separately from or included with a sample, allowing further normalizations, including compensating for sensitivity, variations in input concentration, and variations in wavelength sensitivity.

In addition to modification of optical properties, chemical and fluid flow properties of the cuvette may be modified or controlled by coatings, inserts, gettering elements, microchambers, pore containing elements, filters, or partially permeable barriers. This may include hydrophilic or hydrophobic coatings or structures to improve or reduce fluid flow properties. In other embodiments, chemically reactive patches or gettering agents can be used to bind, absorb, or adsorb contaminating or undesired sample components such as proteins, molecules, or the like. In further embodiments, a surface treatment, surface modification or surface coating such as polyethylene glycol (PEG) may be utilized so as to minimize nonspecific binding. In still other embodiments, chemical functionalization can be used to localize analyte, or chemically reactive coatings, catalysts, structures, nanochambers, or the like can be provided so that the cuvette supports a desired reaction.

To quantify biological and chemical events or to identify a compound, a sample with a particular analyte may be held in the cuvette. Samples can be derived from materials of biological origin, such as tissue samples, blood, sputum, epidermal scrapings, etc., environmental materials such as soil, water, or air samples. A non-exhaustive list of analytes to be detected in a sample includes materials in solid, liquid or gaseous states, and may be comprised of naturally-occurring or synthetic molecules including carbohydrates, proteins, lipids, oligonucleotides, nucleic acids, any organic polymeric materials, inorganic materials, including but not limited to salts, metals, or metal complexes. Liquid solutions include those containing an aqueous, organic or other primary components, gels, gases, and emulsions. Exemplary solutions include celluloses, aqueous solutions, deionized water, blood, physiological buffer, cerebrospinal fluid, urine, saliva, water, and organic solvents.

Positioned below the cuvette may be one or more optical filters, contacting or in close proximity to the cuvette. Generally, an optical filter may be fabricated so that broadband light may be differentially absorbed or reflected, with transmitted light having a significantly different spectrum than the incident light. One common way of manufacturing color filters is to deposit two or more dielectric materials having different refractive indices on a transparent substrate such as glass. Typically, an interference optical filter is obtained if two or more materials having different refractive indices are stacked in several layers having various thicknesses on a glass substrate, wherein thicknesses of a quarter wavelength of the wavelength of interest are frequently utilized. An optical filter fabricated in such a manner can have a desired band characteristic and transmittance. However, close to atomic layer deposition control may be required for best results, many desired bandwidths may be difficult to manufacture, and such interference optical filters are angle dependent.

An alternative approach to generating an optical filter utilizes color filter glass or color photoresists as typically utilized in an RGB camera. Some filters may utilize a combination of interference filters and absorptive glass filters, particularly to provide lower angle sensitivity.

In order to make low cost and improved color filters, use of structurally patterned color filter layers is contemplated. Structural color filters are distinct in that they consist of a single layer that has lateral dielectric contrast, wherein said dielectric contrast may contrast the dielectric constants of different dielectrics, or may contrast the dielectric constants of one or more dielectrics and the dielectric constants of one or more metals, as opposed to the aforementioned interference optical filters which are structured in the out-of-plane direction. Structural color filters are relatively simple and affordable to fabricate; although they do require patterning and deposition or removal steps, low cost and widely available patterning technologies such as lithography can be used, as well as more advanced patterning techniques as nanoimprinting or self-assembly. Typically, a structural color filter can be formed by selective etching or deposition of a single layer deposited by various techniques including sputtering, evaporative coating or other physical vapor deposition techniques, chemical vapor deposition, electroplating or other conventional coating technologies. Examples of structural color filter layers include photonic crystals and plasmonic color filters.

Plasmonic color filters, specifically, consist of patterned layers in which one or more of the constituent materials may be a plasmonic material. The term "plasmonic material" used herein encompasses any material that can support bulk and/or surface plasmons. When light is incident to a plasmonic material, electrons near the surface of the plasmonic material such as metal oscillate in response to the incident electric field, forming a surface plasmon or surface plasmon polariton excitation. The spectral properties of light transmitted by a plasmonic color filter can be significantly modified from that of the incident light and may be controlled by selecting composition, microstructure, thickness, and patterning of the plasmonic material and the surrounding dielectric environment. The composition of the plasmonic material may be selected to accommodate the desired spectrum of light to be transmitted, for example, gold may be selected to transmit visible and near-infrared light while aluminum or silver may be selected to transmit near-ultraviolet light. In some embodiments, all plasmonic color filters may be fabricated using the same plasmonic material composition, thickness, and microstructure while in other embodiments, multiple plasmonic material compositions, thicknesses, and microstructures may be incorporated within or amongst a set of plasmonic color filters.

The plasmonic color filter patterns may be formed by any suitable method. For example, a masking layer may be formed and structures may be defined using photolithography, e-beam lithography, imprint lithography, or focused ion beam milling. The structures created in the masking layer can subsequently be used to create a pattern in the underlying plasmonic material by chemical or physical etching, lift-off methods, or selective growth methods. Alternatively, the patterns may be formed in the plasmonic material without a masking layer by the selective deposition of structures on a prepared substrate or by forming a seed layer on the film and patterning the layer into the structures by electroplating, electroless plating, or any combination of disclosed methods. In other embodiments, a plasmonic material may be directly patterned using focused ion beam milling. In some embodiments, an adhesion layer such as $TiO_2$, $Cr_2O_3$, Ti, Pt, Ni or Cr, may be utilized to better adhere a metal film or films, wherein the thickness may be less than 25 nm, less than 10 nm, less than 5 nm or less than 3 nm. In other embodiments, the metal film or films may be directly adhered to the substrate.

In certain embodiments, auxiliary filters can be used above or below the cuvette, and above or below the structural color filter. Conventional dielectric filters, polarizing filters, absorption filters, or combinations thereof can be used, as well as more sophisticated active filters. In one embodiment, the auxiliary filter comprises a device or mechanism capable of selecting the wavelength composition (or spectrum) of light admitted to the detector. Such emission spectral filters include absorption filters, interference filters, liquid crystal tunable filters, acousto-optic tunable filters, electro-optic tunable filters, gratings, monochromators, and/or prisms, among others. One or more filters having suitable spectral characteristics (e.g., bandpass and band center) may be housed in one or more filter selectors such as a filter wheel or filter slider so that the wavelength composition of the excitation admitted into the cuvette, or emission light admitted to the detector may be changed by rotating or sliding or otherwise placing a preselected filter into the optical path. Any of the filters or filter selectors may be placed under computer control to automate filter selection, which may be further coordinated with excitation wavelength selection. Alternatively, a motorized grating or prism may be utilized with an adjustable slit to select a band center and bandpass respectively.

Emission spectral filters may be used to transmit emission light and block excitation light in photoluminescence applications. Specifically, emission spectral filters with appropriate cutoff wavelengths can separate emitted light from incident (excitation or illumination) light due to differences in wavelength. For example, in conventional photoluminescence assays, the detected (emission) light is of longer wavelength than the corresponding illumination (excitation) light. In contrast, in multiphoton photoluminescence assays (and in anti-Stokes Raman scattering), the detected light is of shorter wavelength than the corresponding illumination light. In the absence of an emission filter, stray excitation light created, for example, by scattering and/or reflection may be detected and misidentified as photoluminescence, decreasing the signal-to-background ratio.

After light passes through the collimator, the cuvette, and various structural color filters or auxiliary filters, it may be detected by a two dimensional sensor. The sensor 50 can include, but is not limited to, conventional pixel or focal plane array (FPA) devices, including a front or back illuminated charge-coupled device (CCD), a photon penetration depth dependent CCD, a photo-diode array (PDA), an avalanche photodiode (APD) array, a PMT array, or a front or back illuminated complementary metal-oxide semiconductor (CMOS) detector. For low cost embodiments, consumer CMOS detectors can be used with suitable modifications. Preferably, such detectors may have a pixel count in excess of the number of plasmonic color filters. Alternatively, a CCD chip can be used for applications requiring greater count accuracy, quantum yield, or binning flexibility. The sensor may be cooled or temperature stabilized. The sensor may be a monolithic sensor, or may be a hybrid sensor with different sections of the sensor utilizing different materials (such as silicon, InGaAs, HgCdTe), such that the different sections may have different wavelength quantum efficiencies, or the sensor may be a sensor assembly wherein multiple sensor chips may be integrated into a single sensor, which may be effectuated utilizing a PCB or hybrid assembly. Monochrome detectors can be used, or alternatively, detectors with conventional Bayer filters or other custom absorption filters can be used. Other detectors are possible, including long wavelength bolometers or the like.

An optional undercoat or "spacer" layer(s) may also be utilized across the whole surface of the sensor. Such a layer can provide a electronic isolation functionality, function as an adhesion layer, support planarization of the sensor (if it is substantially non-uniform), provide a protective barrier layer that protects, for example, the sensor from unwanted conductive metal diffusion. In certain embodiments, the spacer can include a long wave pass filter to select the correct diffractive order, or to reject excitation light in a fluorescent device. In still other embodiments, the spacer layer can contain a phosphor including lanthanides, or other rare earth elements or transition metals, or lanthanide complexes such as chelate stabilized lanthanides or other rare earth complexes or transition metal complexes, or quantum dots to act as an wavelength up-conversion or down-conversion layer. This can allow an improved match between the wavelength of the spectroscopic signal and the sensitivity band of the sensor. In some embodiments, a wavelength up-conversion or down-conversion layer may be positioned in the immediate vicinity of a plasmonic color filter such that enhanced electromagnetic field intensity can be used to improve the efficiency of nonlinear conversion processes. For example, a lanthanide-based phosphor layer may be positioned within 500 nm of the plasmonic color filter to provide near-field coupling between surface excitations such as surface plasmon polaritons and the phosphor layer. In some embodiments, a spacer can separate a sensor from a cuvette and may provide chemical and/or mechanical protection. An overcoat layer may additionally improve optical, thermal or electronic matching between a sensor and a cuvette, and may provide antireflection, electrical or thermal impedance matching.

The transmitted light from each plasmonic patch 22 can be addressed to one or more pixels on the focal plane array. Typically, pixels on the sensor may be correlated, associated with, physically aligned with, or matched to specific pattern patches 22 of plasmonic color filter(s). In one embodiment, pixels on a sensor may be associated with transmitted light selectively using an algorithm incorporating calibration measurements performed after the assembly of the spectroscopy system and/or after the coordination of a sample to be examined within the system. For example, a filter can be used to identify pixels associated with transmitted light on the basis of an intensity threshold with a geometric shape invariant related to the geometry of specific pattern patches. One pixel can be matched to one filter pattern, or alternatively, multiple pixels can be illuminated by one patch.

A spectral measurement of the optical extinction of the cuvette 40 contents may be correlated to the intensity signals from spatially distinct pixels. Suitable linear algebra calculations can associate observed intensity to the signal intensity via a filter transfer function matrix, which may further include data for the dark current of the sensor, background signal levels without an excitation being provided, and baseline signal levels when there is no sample present. Multiple independent "micro spectrometers" can thus be formed, with each micro spectrometer associated with separate chambers including control and sample chambers, or multiple independent micro spectrometers may be associated with different regions within a single chamber, wherein the different regions may have different associated reagents. In still other embodiments the cuvette can support structures or coatings that provide a gradient of diffusion, such that the different regions may measure different reagents in a sample.

Figure 2:
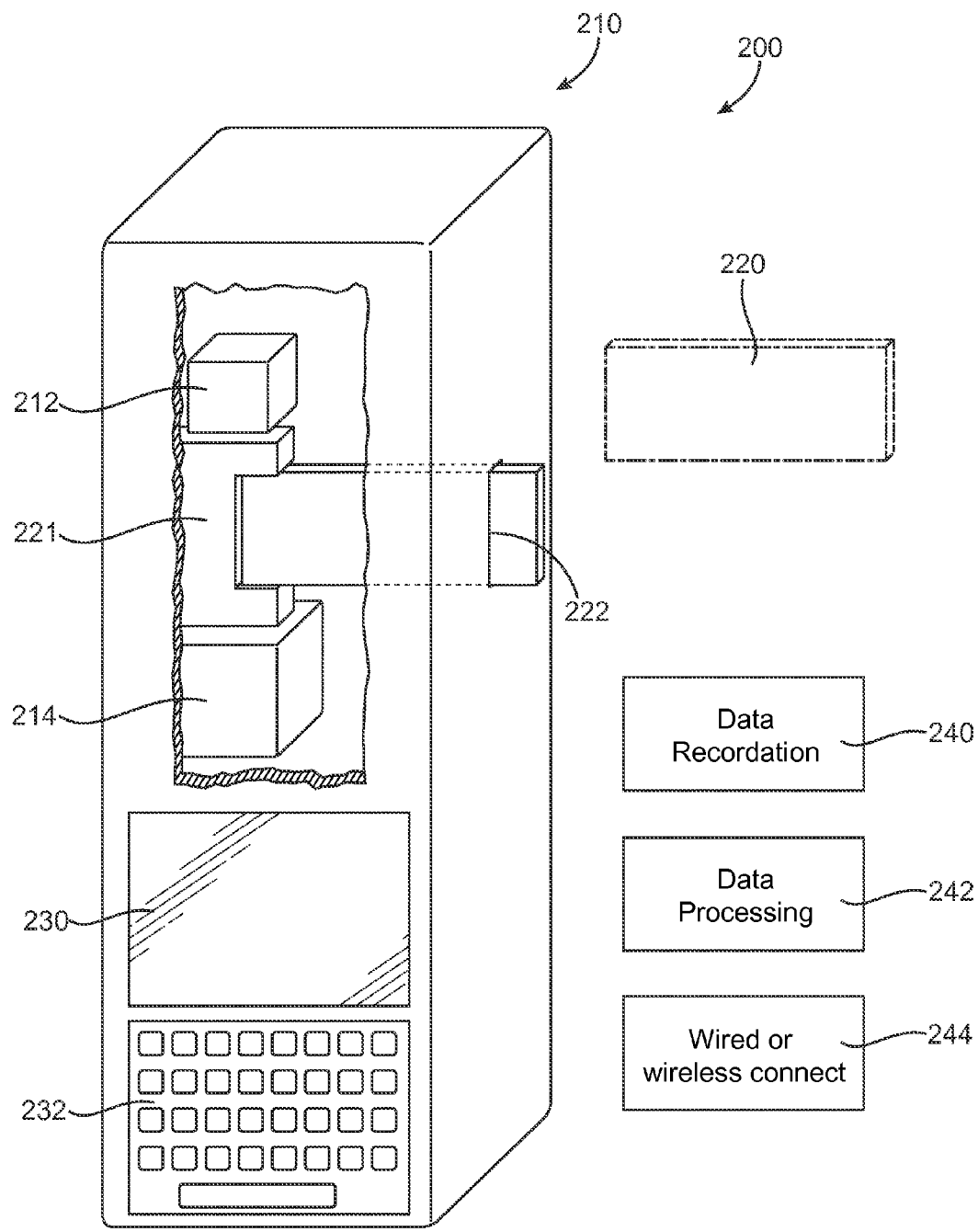
FIG. 2 is a cartoon illustrating a spectrometer system, including electronic data processing, recordation and display, and transmission of information to local or remote sites.

FIG. 2 illustrates a portable, handheld spectrometer system 200, with an optoelectronic reader 210 (partially broken away to illustrate internal systems) and a cartridge 220 capable of being inserted into reader 210 through an access port 222. Such a portable system can be used as a mobile or wearable device to monitor personal health, for high resolution color monitoring for color input, display and output devices, or as an environmental monitoring sensor such as for water or air quality sensors. The spectrometer system 200 may be of particular use for low resource settings such as a remote village, and can optionally be used to provide individuals with information relating to nutrition/liver panels, protein markers which indicate severity of trauma or disease, or even direct identification of infectious diseases. Other applications include long term, low cost monitoring of diabetics (particularly for non-glucose markers), individuals taking costly or concentration sensitive drugs (e.g. anti-clotting drugs such as warfarin), or other suitable biomedical applications.

In the illustrated implementation, the reader 210 includes a lighting subsystem 212, a cartridge holder 221 for holding cartridge 220, and a detector/electronics subsystem 214. Preferably lightweight, affordable components such as an integrated OLED, LED, a xenon flash lamp or other inexpensive light sources may be used either alone or in combination in the lighting subsystem 212. Similarly, low cost computational electronics and software, optical control electronics, and a CMOS or CCD based camera chip may be used in the detector electronics subsystem 214.

Local display of status, results, and error messages or the like may be afforded by optional display 230. OLED, LCD, bistable displays (electronic paper or similar) or other conventional displays can be used. Optional input pad 232 can be a keyboard, touch sensitive element (which may be integrated as part of the optional display 230), or similar to provide for user input. In certain embodiments, a wired or wireless connect subsystem 244 can be used to connect to a user interaction device such as a smart phone (not shown), external or integrated data processing device 242 and external or integrated data recordation device 240. Optionally, data and control signals can be received, generated, or transported between varieties of external data sources, including wireless networks or personal area networks, cellular networks, or internet or cloud mediated data sources. In addition, spectrometer 200 may include a source of local data (e.g. a hard drive, flash memory, embedded DRAM, or other known data retention systems) that can allow for firmware or software updating, and allows for data storage or control by direct user input or user-specified preferences or protocols.

The cartridge 220 may be a disposable, affordable component. Cartridge 220 can contain the passive elements of the microfluidic system including flow channels and cuvettes, chemical reagents, and metallic optical components including mirrored surfaces. In certain embodiments, structural color filters such as plasmonic filters can be directly attached or formed on the cartridge. In other embodiments, structural color filters and auxiliary bandpass or high pass, absorption or dielectric filters can be positioned adjacent to cartridge. As will be appreciated, chemical reagents and optical components can be optimized for a specific set of spectroscopic assays. This allows the functionality of the device to be changed simply by swapping the cartridge and software. In some embodiments, the cartridge may be reusable. In some embodiments, microcuvette cartridges disclosed in a commonly-owned U.S. patent application Ser. No. 14/095,971, entitled "Microcuvette Cartridge", filed concurrently herewith, which claims benefit of U.S. Provisional Application Nos. 61/745,503, filed Dec. 21, 2012, and 61/778,315, filed Mar. 12, 2013, may be used for the cartridge 220. That U.S. patent application is hereby incorporated by reference in its entirety.

In some embodiments, the cartridge can include a coded identification, which may be associated with a protocol, thus permitting the swapping of the software to be effected automatically with the swapping of the cartridge. The coded identification may be a 1D or 2D optical barcode, a DNA barcode, an RF barcode, semiconductor barcode, or any other kind of barcode. The protocol may be stored in the spectrometer, in an external data storage device, or may be accessed from an external database, wherein the protocol associated with a particular cartridge may be directly associated therewith. In alternative embodiments, the protocol may be directly stored with or in the cartridge, and may be stored in flash memory, printed thin film organic memory, or any other non-volatile memory. The spectrometer may access the stored protocol when the cartridge is changed.

Advantageously, spectrometers according to the present disclosure can be used to track biological indicators of single or multiple patients, using either multiple cuvettes or high throughput cleanable cuvettes. The low cost and ease of use allows for repetition and redundancy to check accuracy, or can allow for a time series of samples to be tested over the course of minutes, hours, days, weeks, or months. Alternatively, different analyte targets can be tested using the same or different samples by selecting an appropriate combination of light source, filters, and processing schemes.

Figure 3A:
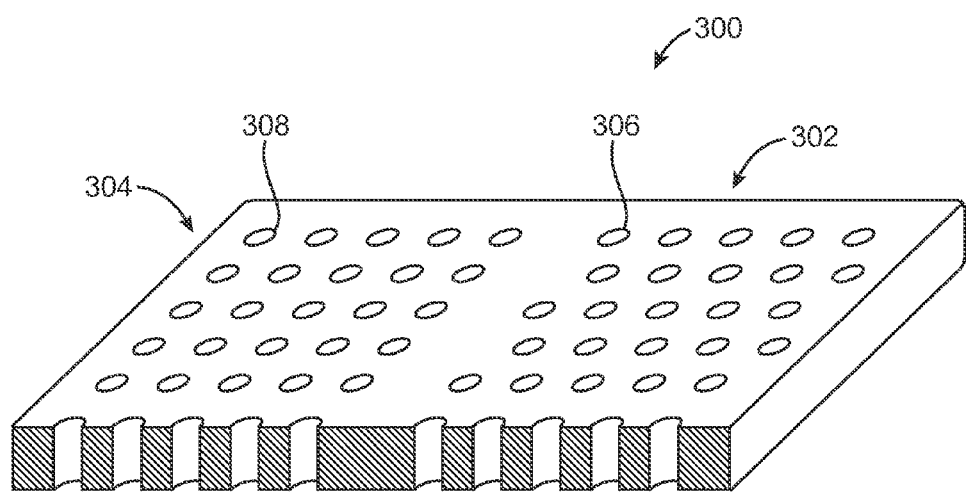
FIG. 3A illustrates a cutaway perspective view of a structural color filter including plasmon resonance elements, with a range of preferred structures being shown.

FIG. 3A is perspective partial cutaway view of representative structural color filter (SCF), which in this embodiment is a plasmonic filter set 300 composed of multiple types of patterned metallic films. The plasmonic filter set 300 comprises one or more patterns, herein referred to as patches of plasmonic filtering regions, of which representative hexagonal pattern 302 and rectilinear pattern 304 extend in defined two-dimensional patterns across the surface. Thus, the rectilinear pattern 304 and the hexagonal pattern 302 are examples of plasmonic patches that may be used as patches 22 shown in FIG. 1. The filtering regions can include various apertures 306 and 308 in a metallic film, optionally filled with dielectric material. In operation, a certain percentage of light striking the plasmonic filter may be partially reflected to enable passage back through a cuvette, and a certain percentage may be also differentially filtered and transmitted through the plasmonic filter for readout by a suitable sensor.

The apertures 306 and 308 in the film can be formed using known deposition, lithography and etching techniques. It should be understood that the circular, rectangular, square, ellipsoidal arcuate, triangular, cylindrical, pyramidal, cross-shaped, trapezoidal, conical, bowtie, annular and combinations thereof, are non-limiting examples and that other shapes of the apertures are contemplated.

The surface plasmon filter set, which can be used as the filter set 20 of FIG. 1, may support one or more of the patches 302, 304 and other patterned patches as described below, with each patch acting to filter light based on various properties, including wavelength or polarization angles, and each patch may include a number of plasmonic unit structures in an array.

Radial symmetries utilizing any of the aforementioned apertures or combinations thereof may be utilized. Said combinations may be configured to effectualize a single effective wavelength with greater sensitivity, or may be configured to effectualize multiple wavelengths to be associated with a single "micro spectrometer", or a combination thereof may be utilized. Said apertures may be configured to effectuate a dipole field, or a multi-pole field.

Figure 3B:
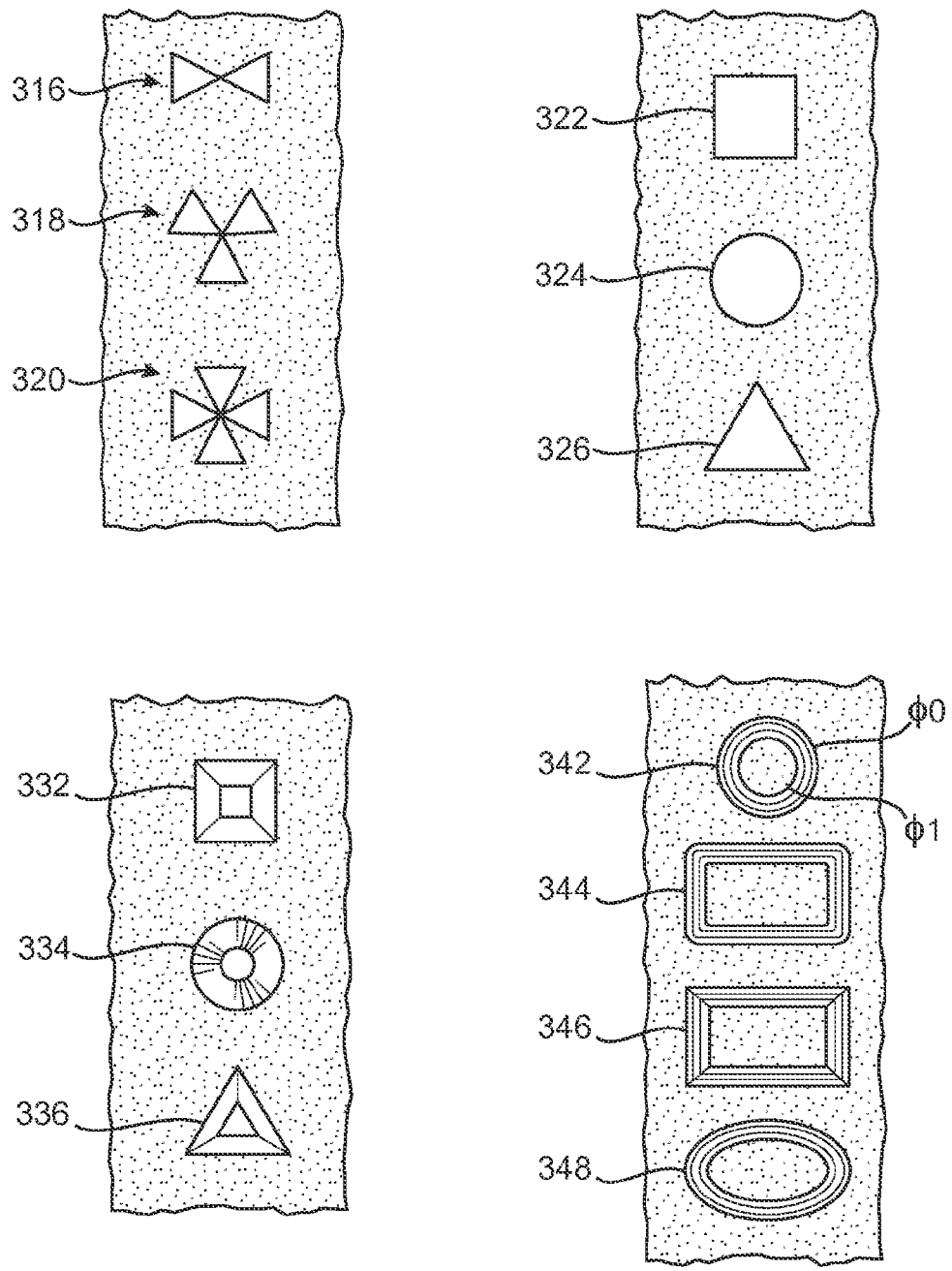
FIG. 3B illustrates several types of plasmonic structures.
Figure 3C:
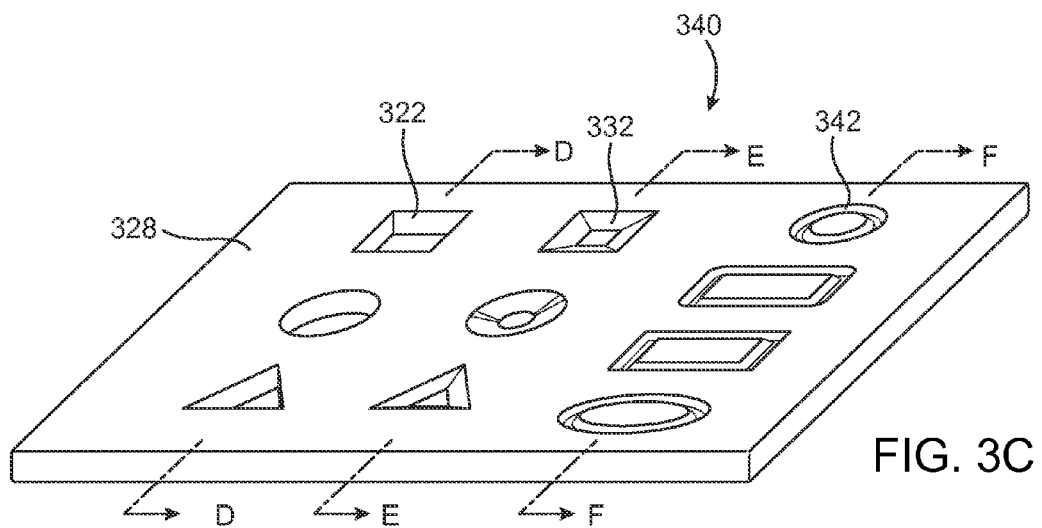
FIG. 3C illustrates a perspective view of plasmonic structures.
Figure 3D:
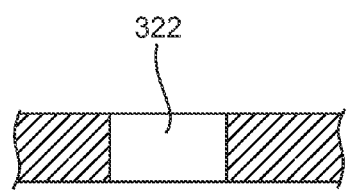
FIG. 3D illustrates a cross section of a plasmonic structure.
Figure 3E:
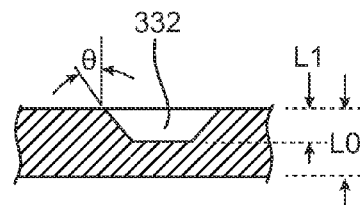
FIG. 3E illustrates a cross section of a plasmonic structure.
Figure 3F:
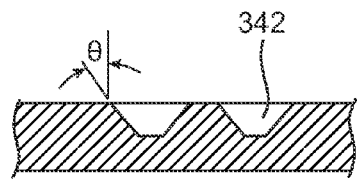
FIG. 3F illustrates a cross section of a plasmonic structure.

FIG. 3A shows circular penetrating holes as the unit plasmonic structure forming the respective patterns 304 and 302. The individual unit that forms the pattern is not limited to the circular hole. FIG. 3B illustrate examples of other individual plasmonic unit structures that can form plasmonic patches. In FIGS. 3B and 3C, each of the structures 316, 318, 320, 322, 324, 326, 332, 334, 336, 342, 344, 346, and 348 represents a plasmonic unit structure that can form a plasmonic patch alone or that can be arranged in a certain pattern such as rectilinear and hexagonal patters 304 and 302 to constitute a plasmonic patch. As shown on the lower right in FIG. 3B, in some embodiments, a radially symmetrical coaxial resonant plasmonic structure may be fabricated. Such a structure may be described by the use of five parameters including: the slope of the outer sidewall angle $\theta$ (shown in FIG. 3E and FIG. 3F), the thickness of the metal surrounding the etched structure L0 (shown on the right in FIG. 3E), the depth of the etch into the metal L1 and thus the thickness of the center metal structure (shown on the right in FIG. 3E), the outer diameter of the etched torus $\phi_0$, and the inner diameter of the etched torus $\phi_1$.

In some embodiments, other radial symmetries may be utilized as illustrated in the top left section of FIG. 3B, wherein two 316 three 318, and four 320 aperture plasmonic structures are illustrated. In the top right portion of FIG. 3B, further illustrated in left hand portion of FIG. 3C and in cross section 3D are square 322, circular 324, and triangular 326 through etched plasmonic structures. In the lower left portion of FIG. 3B, further illustrated in middle portion of FIG. 3C and in cross section 3E are square 332, circular 334, and triangular 336 partially etched plasmonic structures with sidewall angle $\theta$. In the lower right portion of FIG. 3B, further illustrated in right portion of FIG. 3C and in cross section 3F are circular 342, rounded rectangle 344, rectangle 346 and oval 348 partially etched plasmonic structures with center "islands" and sidewall angle $\theta$.

Figure 3G:
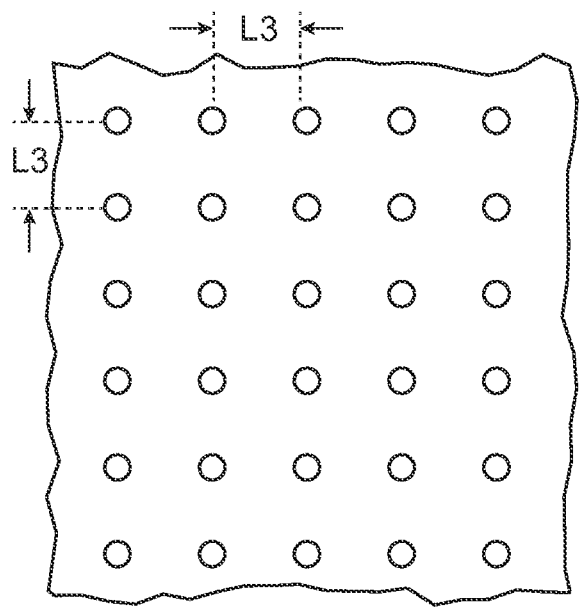
FIG. 3G is a top view of a plasmonic filter.
Figure 3H:
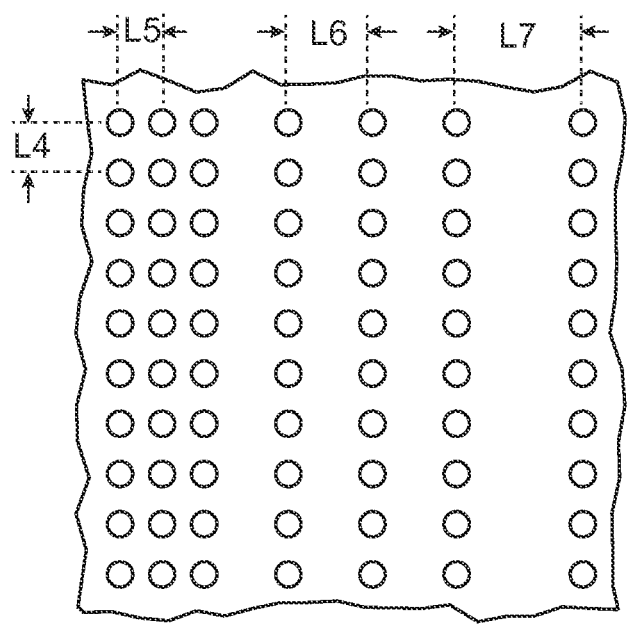
FIG. 3H is a top view of a plasmonic filter.

In some embodiments as illustrated in FIG. 3G, the spacings between said plasmonic structures may be a fixed spacing, such as a distance L3. In other embodiments as shown in FIG. 3H, the spacings between said plasmonic structures may vary among the patches or within a single patch; said variable spacings may vary associated with a continuous function or discontinuous function in one or both axes, and the function may be different in the different axes, or may vary in one axis and be fixed in the other axis. In FIG. 3H, a fixed spacing L4 is utilized in one axis, while the other axis has a discontinuous function utilizing three spacings, L5, L6 and L7. As described above, these variations in spacing may be distributed among different patches or may be provided within a single patch. In some embodiments, the wavelength and or bandpass of plasmonic structures within a patch may be the same, or the wavelength and or bandpass may vary in a known manner.

Figure 4A:
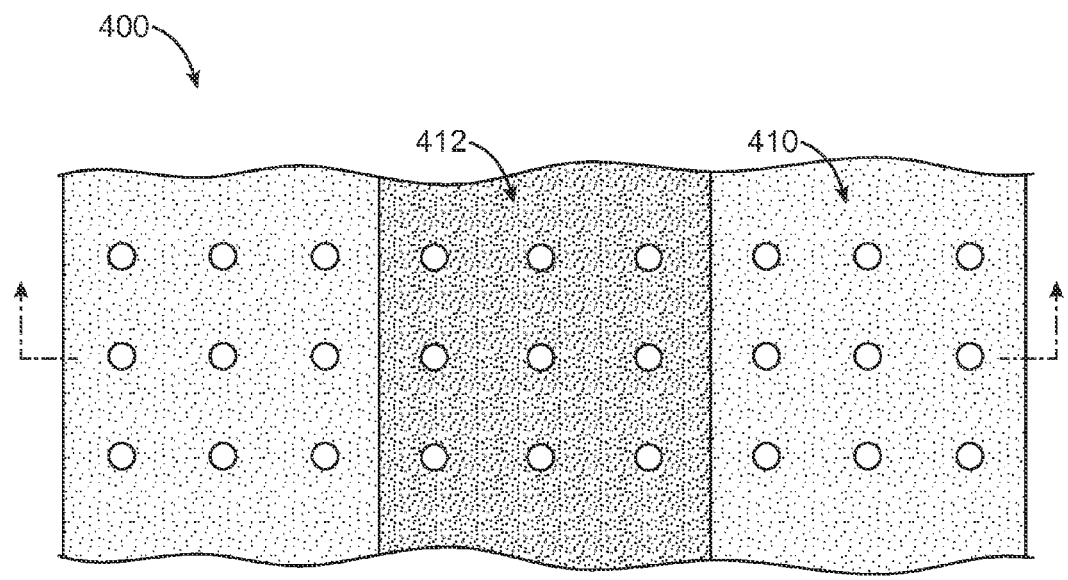
FIG. 4A is an example of a stacked filter structure.
Figure 4B:
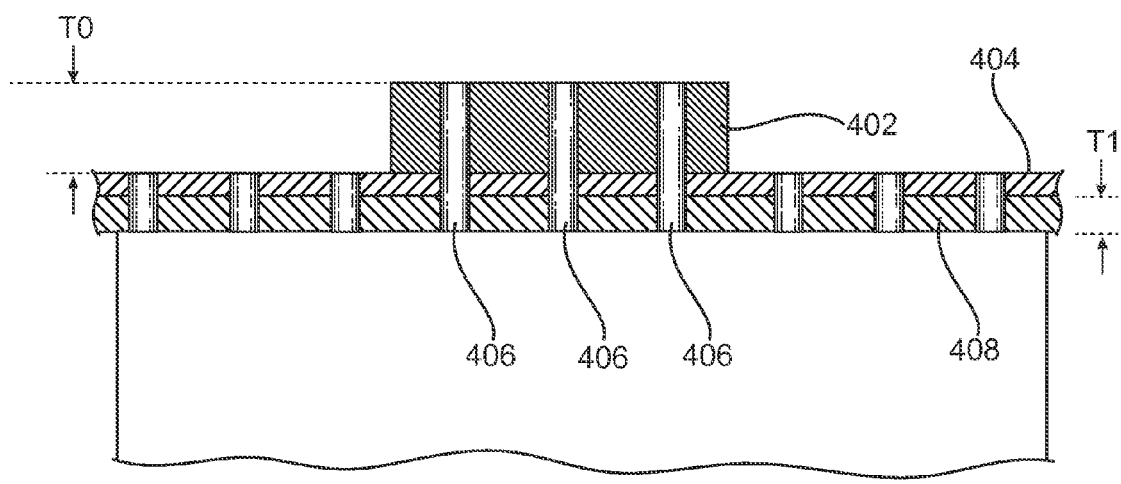
FIG. 4B illustrates a cross section of a stacked filter structure.

In contrast to single layer structural color filters disclosed with respect to FIG. 3, multilayered structures may be adopted to form various plasmonic filter patches having a wide range of differing optical properties. FIGS. 4A and 4B show an example of such a multilayer structure. Such filters may be particularly useful for modification of light to provide filtering, down converting, two photon up-converting, focusing of light energy or otherwise increasing energy density, and/or redirecting light energy. As can be seen in the FIG. 4, a focal plane array may be covered with a deposited silver (Ag) layer 408 which may have a thickness T1 of approximately 50 to 200 nm thick, with 100 nm being typical. The Ag layer 408 may be encapsulated with a transparent (for the relevant wavelengths) aluminum oxide ($Al_2O_3$), silicon nitride ($Si_3N_4$) or other chemically resistant layer 404, and lithographically patterned to create plasmonic patch/filter 410. On top of the foregoing layers, aluminum or other desired metal film 402 can be formed in specified areas and with defined patterns with a thickness T0 of approximately 30 to 150 nm thick, with 70 nm being typical to create plasmonic patch/filter 412. Said forming of said metal film 402 may utilize a process such as a CMOS metalization process. A cleaning process may then be performed. Additional lithographic or other processes can also be employed to form plasmonic patch/filter 412 through all the layers. Said additional processes utilized to form plasmonic patch/filter 412 may include Focused Ion Beam (FIB) milling, Inductively-Coupled Plasma (ICP) etching, liftoff, or any other appropriate fabrication process. Because of the multilayered structure, some patches may be formed with a single layer structure (patch 410 in FIG. 4A) with an appropriate pattern of appropriate plasmonic unit structures, examples of which are depicted in FIGS. 3A-3H, and other patches may be formed with a multilayered structure (for example, the two-layer structure of patch 412 in FIG. 4A) with an appropriate pattern of appropriate plasmonic unit structures, thereby expanding the design freedom. Therefore, plasmonic patches/filter having a wide range of desired optical properties can be designed and manufactured.

To further understand various aspects and advantages of structures and methods disclosed herein, the following examples are provided to illustrate particular features of practical spectrometry components, modules, subsystems, and full systems suitable for a range of applications.

EXAMPLE 1

Figure 5A:
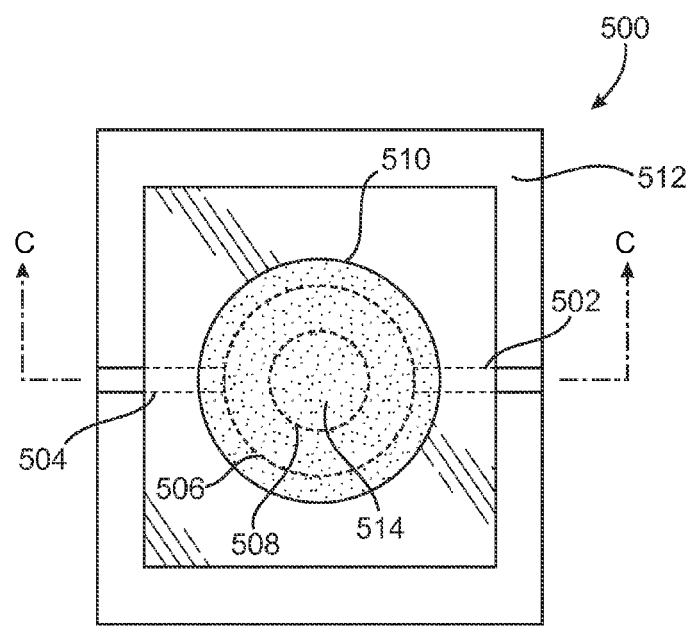
FIGS. 5A-5E are examples of built-in cuvette flow chambers.

A single cuvette with PDMS flow system is illustrated in several alternative forms in FIG. 5A-FIG. 5E. FIG. 5A shows a top view of a single microcuvette assembly 500 showing a single microcuvette 514, which may also be part of an array of microcuvettes (not shown). Said single microcuvette assembly 500 may have an input microfluidic channel 504, and an output microfluidic channel 502, which may be etched or formed in the substrate 512 (which may be a part of underlying substrate 540, or may be added, affixed or bonded to underlying substrate 540), and an optional optical filter 510. A plasmonic filter set, similar to filter set 20 of FIG. 1, which may be a structural plasmonic set formed of a patterned Au metal film, for example, or a single plasmonic filter may be disposed at the bottom separately or as a part of the microcuvette assembly 500. The thickness of said Au metal film may be 10 to 500 nm. Said substrate may comprise plastics such as Thermanox™ vinyl, cellulose acetate, or glasses such as borosilicate glass, fused silica or quartz, soda lime, or silicate glass. Said microcuvette assembly 500 may further have a microcuvette 514 formed in a substrate 512 between said input microfluidic channel 504 and said output microfluidic channel 502, and the microcuvette bottom 508 may have a smaller diameter than the microcuvette top 506, wherein the microcuvette bottom 508 may have diameter of 100 μm, but may be of any diameter from 100 nm to tens of millimeters.

Figure 5B:
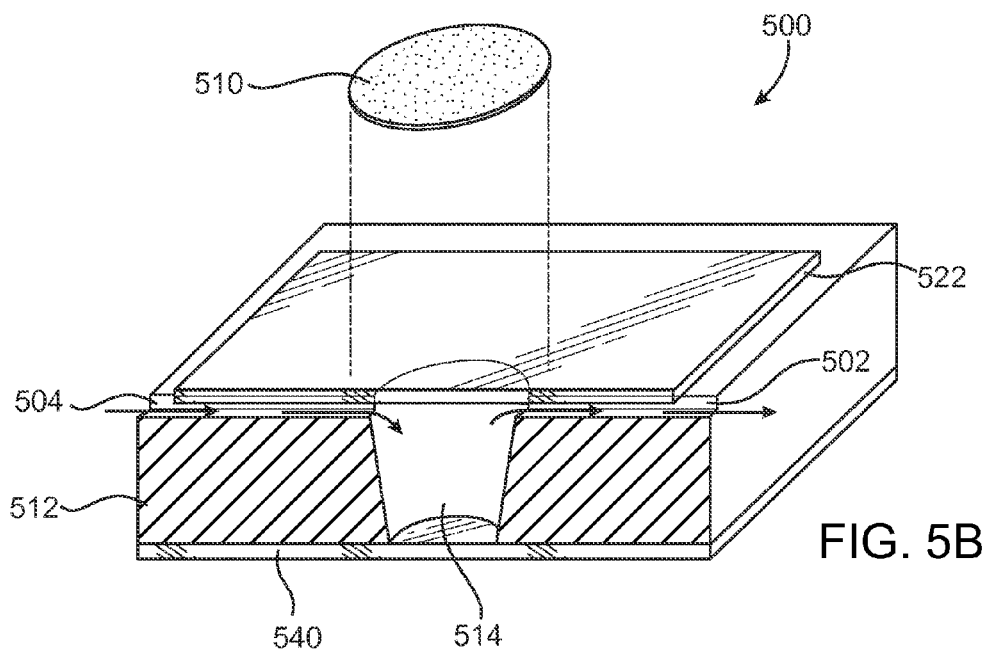

FIG. 5B is an isometric view of said microcuvette assembly 500, showing the fluid flow in input microfluidic channel 504 and output microfluidic channel 502, and further showing cover 522 forming the top of said channels and micro cuvette 514.

Figure 5C:
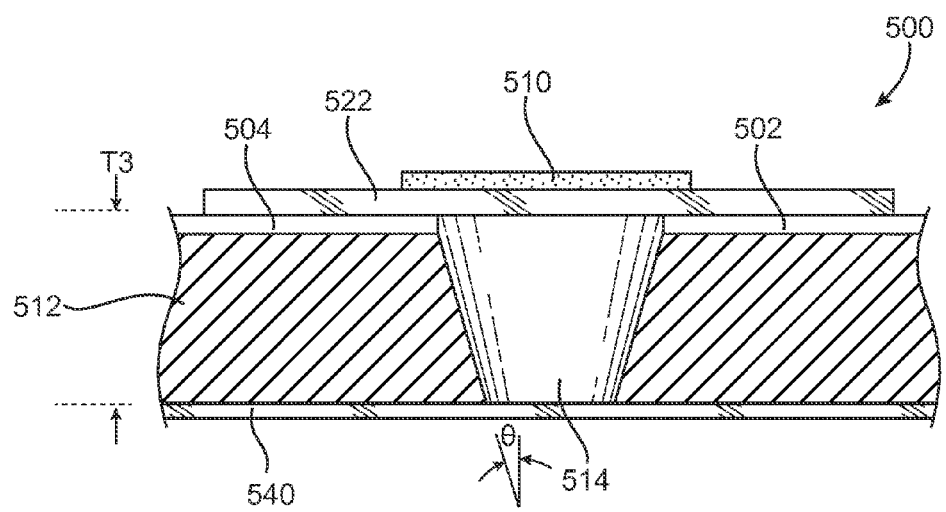

FIG. 5C is a cut away view of FIG. 5A, which illustrates a cross section of said microcuvette assembly 500, and further illustrates the sidewall angle θ which results from the greater diameter of the microcuvette top relative to the microcuvette bottom. The thickness (and thus the depth of microcuvette 514) T3 of the substrate 512 is shown, which may be 1.1 mm. Said microcuvette 514 is also shown with cover 522, which may comprise glass or plastic materials as herein described, and which may be anodically bonded to the substrate 512, or may be adhesively affixed or otherwise bonded. The monolithic optical filter 510 may be fabricated on the cover 522 prior to assembly with the substrate 512, or may be fabricated on the completed assembly comprising the substrate 512 with microcuvette 514, input microfluidic channel 504, and output microfluidic channel formed therein, and bonded sealed or otherwise affixed to the cover 522. The microcuvette may be formed utilizing an additive process, or may be etched from an underlying substrate 540; if said microcuvette is etched from an underlying substrate, the substrate 512 and the underlying substrate 540 may be a single part.

Figure 5D:
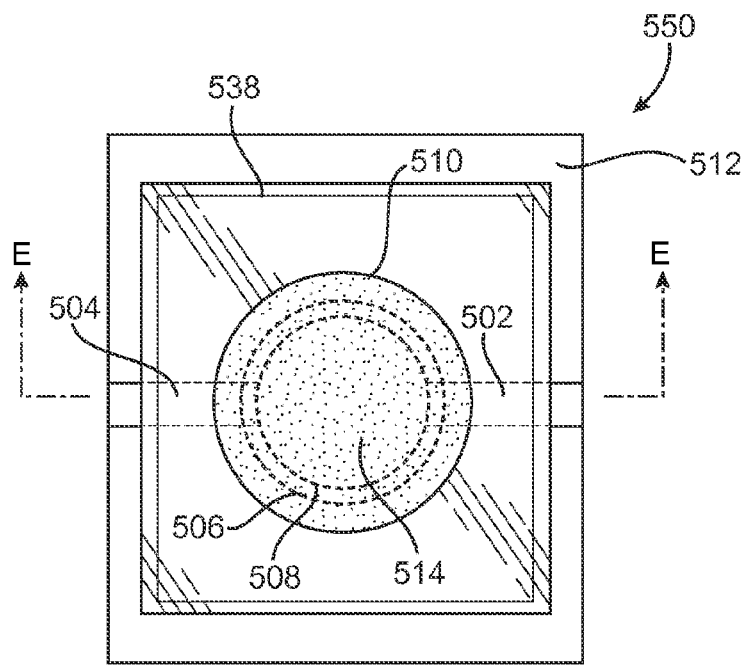
Figure 5E:
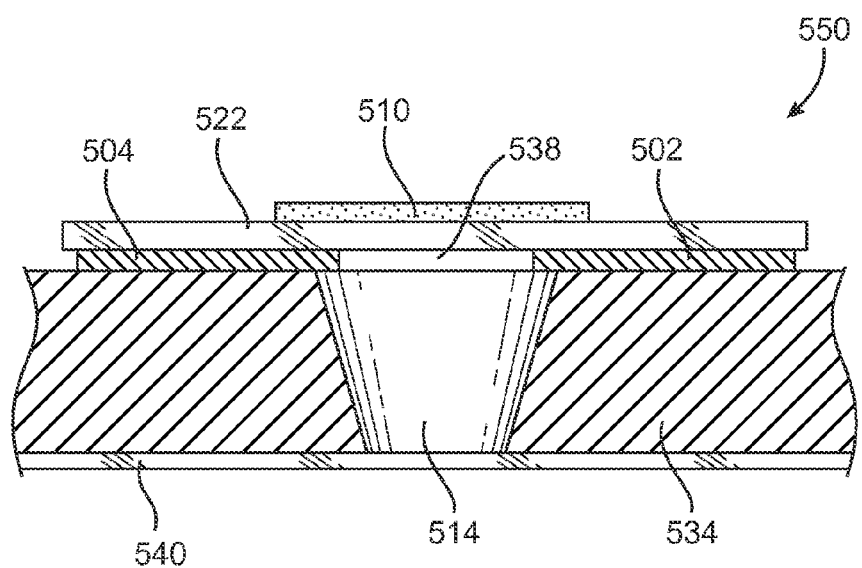

FIG. 5D illustrates an alternative microcuvette assembly embodiment 550, wherein the cover 522 (as seen in FIG. 5E) may be sealed and affixed to the substrate 534 utilizing a PolyDiMethylSiloxane (PDMS) layer 538, which may further form and comprise input microfluidic channel 504, output microfluidic channel 502, and may include an aperture in PDMS layer 538 above microcuvette 514 so that there is no refractive index change between plasmonic structure 510 and microcuvette 514.

EXAMPLE 2

Figure 6:
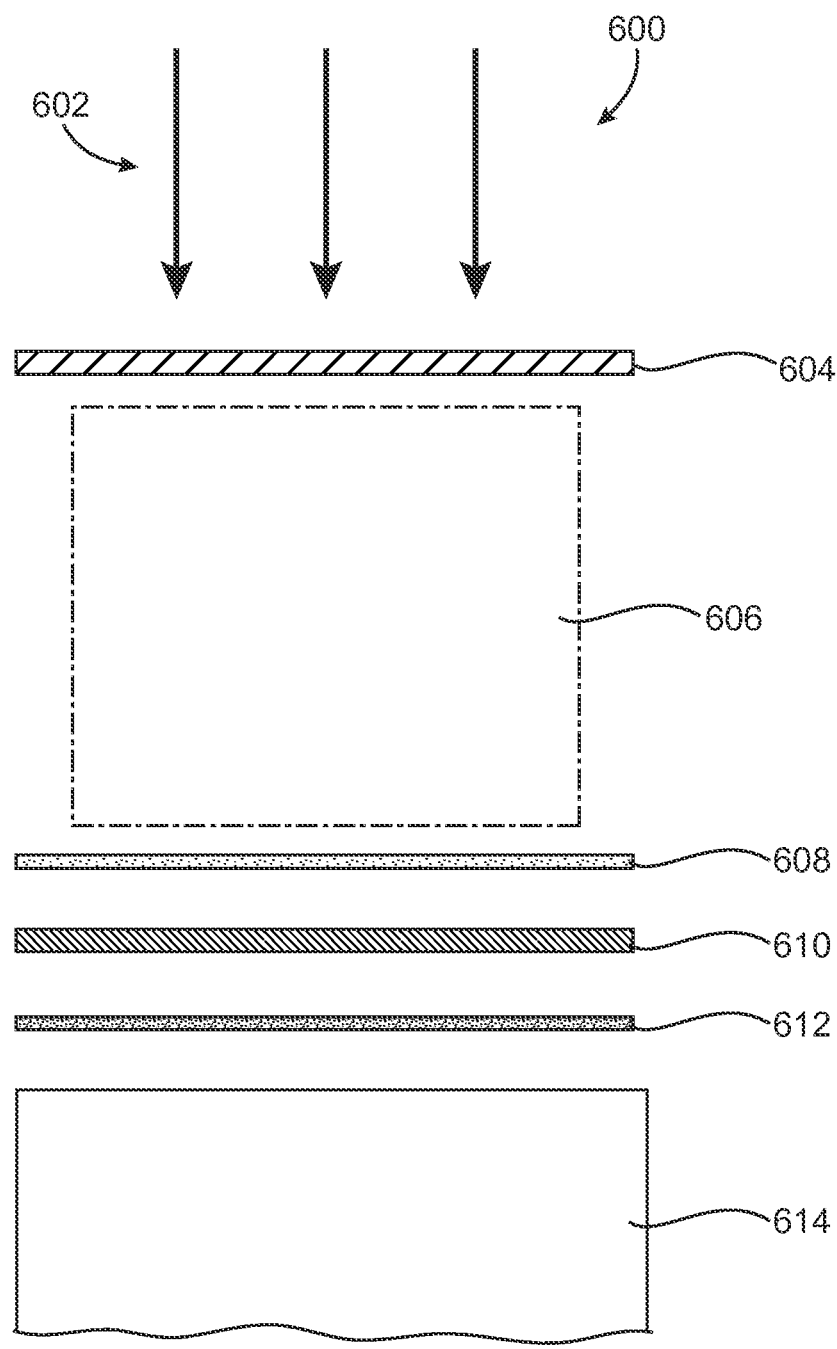
FIG. 6 is an example of a system supporting auxiliary polarizers, narrow and broad bandpass filters.

A disposable cuvette with multiple filters is illustrated in FIG. 6. FIG. 6 shows a cuvette 606 with a first coated surface comprising at least an array of plasmonic color filters 610 and a second opposed surface 604 optionally coated with one or more of a broadband antireflection coating, a UV rejecting layer, and a partial mirror. Said first coated surface may further optionally comprise additional undercoating filter 612 and or additional overcoating filter 608. Substantially collimated light 602 which may be broadband, such as having a Full Width Half Maximum (FWFM) or 40 nm, 20 nm, 10 nm or less, and may have the intensity and polarization controlled, passes through an absorbing sample specimen (not shown) in the disposable cuvette 606 and analysis of transmission through the plasmonic color filter array 610 onto the detection surface of the sensor 614 may provide spectral analysis. The detection surface may comprise an array of discrete photodiodes, or any other type of detector, such as CMOS sensors, CCDs, as described herein. Alternatively, the outgoing face may be imaged using a fiber bundle (not shown) directed onto a remotely located detection surface of a sensor.

EXAMPLE 3

Figure 7:
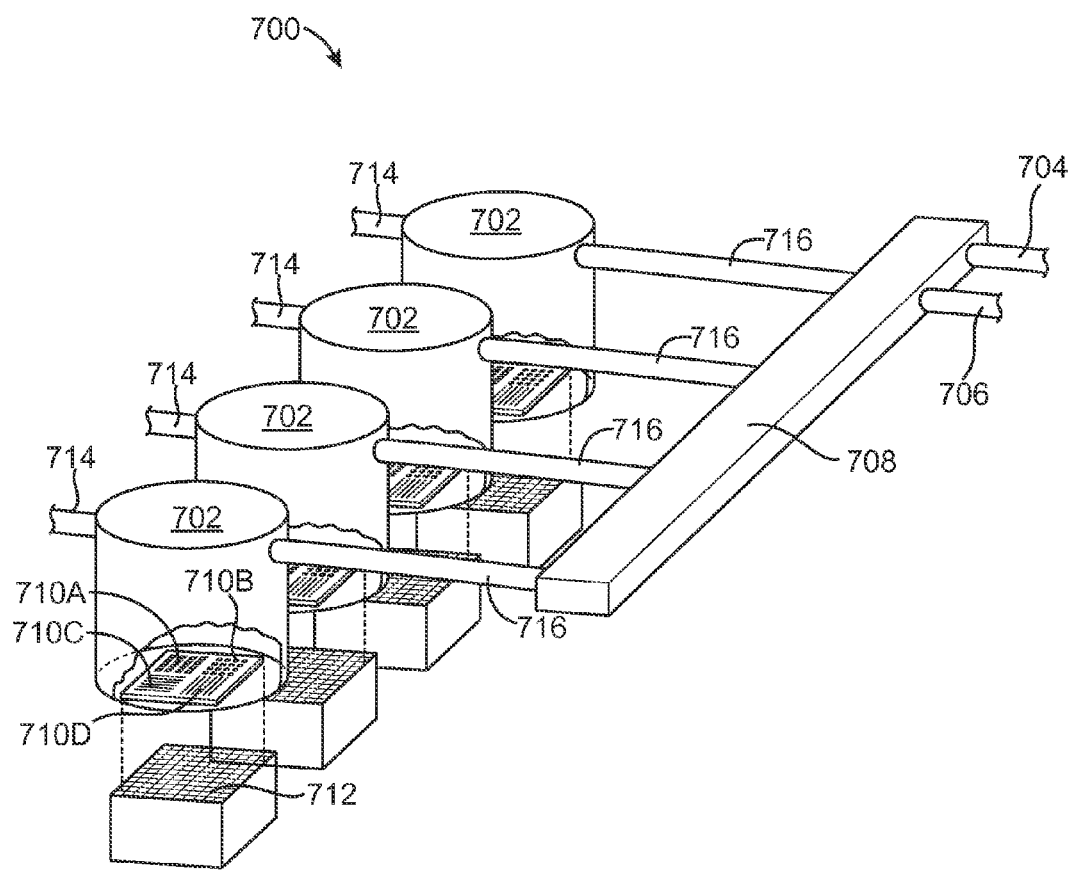
FIG. 7 is an example of a multicuvette laboratory system.

A multiple cuvette laboratory system 700 is illustrated in FIG. 7. The multiple cuvette system 700 may comprise an array of cuvettes 702, which may be a linear array as shown, or may be a 2D array, an array with radial symmetry, a spiral array, and may be a regular or irregular array. Said multiple cuvette system may further comprise a fluidic system 708 which may have a sample input 706, a diluent input 704 which may be utilized to dilute said sample, and various valves (not shown) as needed to control the flow of said sample and diluent to the different cuvettes 702 through respective pipes 716. Additional inputs (not shown) to the fluidic system 708 may include additional inputs for additional samples, reactants, buffers, lysis agents, and other reagents as needed for an assay.

Each cuvette may have multiple patches 710A-710D for observing different wavelengths, or may have multiple patches intended for observing the same wavelength. As previously described herein, each patch may be constructed of a pattern of plasmonic structures constituting a plasmonic filter/patch that has designed transmission characteristics. Light transmitted through an array of such plasmonic filters/patches 710A to 710D may be received by multiple pixels in a sensor 712 associated thereto, so that changes in the transmission of the spectra may be detected from the two dimensional pattern created by the transmission of the plasmonic filter.

A multiple cuvette system 700 may be utilized for absorbance studies, fluorescent experiments, M×N studies wherein M may represent the number of different samples, and N may represent the number of different reagents or concentration of reagents. Said M×N studies may be utilized for drug efficacy combinatorial screening (high throughput binding assays for drug discovery), Real Time PCR assays, or any other type of M×N assay. In some embodiments, small numbers of cells, which may include single cells, and which may be sorted or characterized as to cell type may be utilized so that the response of single cells or groups of the same cell type may be measured as to the response to a putative drug target or to measure one or more gene expression levels for a single cell or a small group of cells of the same type of call. In other embodiments, the cuvettes may be utilized in a digital PCR assay or other counting assay, where the number of cuvettes that have one or more moieties of interest may be observed and counted.

As described above, each of the plasmonic patches/filters may be formed of an array or a pattern of multiple plasmonic unit structures. The terms "plasmonic structure," "plasmonic unit structure" and like terms used herein encompass any structures or features that can generate plasmons in response to some optical interactions. Regarding the layout of the array or pattern formed by the plasmonic structures that constitutes a plasmonic patch/filter, various patterns can be designed to generate desired transmission characteristics. For example, a variety of patterns as disclosed in a commonly owned PCT International Application No. PCT/US2013/072930, entitled "Plasmonic Projected Diffraction Sensor", which designates the U.S. and claims benefit of Provisional Application No. 61/762,818, filed Feb. 8, 2013, may be used by appropriately designing the dimensions and material to meet target transmission characteristics. That PCT International Application is hereby incorporated by reference in its entirety.

The plasmonic filter sets, or more broadly, filter sets (corresponding to the plasmonic filter set 20 of FIG. 1, for example) as disclosed in this disclosure are constructed of a plurality of filter patches (patches 22 of FIG. 1, for example), each of which has known, measurable, or designed transmission characteristics. Therefore, by measuring the intensity of the light that has passed through the respective filter patches, information on the spectrum of the light entering the filter set can be obtained by an appropriate algorithm. The spectrum can be reconstructed at a resolution that is determined by the number of the filter patches and the transmission characteristics of the respective filter patches. In some applications where target wavelengths are known in advance, for example, the resolution for the wavelengths adjacent to such target wavelengths can be increased by appropriately designing transmission characteristics of the respective patches. The data processing algorithm for these purposes can be implemented in software and/or hardware installed as a part of the system.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those ordinarily skilled in the art. Accordingly, the specification and drawings are to be regarded in an illustrative rather than a restrictive sense.

What is claimed is:

1. A spectrometer system comprising:
a light source and a two dimensional sensor, the two dimensional sensor having a plurality of light-receiving pixels,
a collimating element configured to collimate said light from said light source to provide collimated light,
a cuvette having a first and second at least partially mirrored surfaces arranged to contain a fluid sample, wherein said collimated light from said light source is directed through said cuvette, and
a plasmonic filter set including a plurality of plasmonic filter patches formed on a substrate, the plasmonic filter set positioned after said collimating element and before said two dimensional sensor, wherein each one of said plasmonic filter patches comprises dielectric and metallic regions configured to differentially transmit selected wavelengths of said collimated light received from said collimating element to corresponding one or more of pixels among the plurality of light-receiving pixels of said two dimensional detector that are designated to said one of the plasmonic filter patches,
wherein said selected wavelengths of at least some of the plurality of plasmonic filter patches differ from each other so that intensities of light received at said one or more of the designated pixels through respective ones of said at least some of the plurality of plasmonic filters patches indicate spectroscopic information of the fluid sample.

2. The system of claim 1, wherein said plasmonic filter set is formed on said sensor.

3. The system of claim 1, wherein said collimated light is angled relative to said partially mirrored surfaces such that said collimated light interacts with said plasmonic filter set more than once.

4. The system of claim 1, wherein said dielectric and metallic regions of said plasmonic filter patch are formed so as to be substantially coplanar.

5. The system of claim 1, wherein said collimated light is perpendicular to said partially mirrored surfaces.

6. A system which comprises multiple systems of claim 1, wherein each of said multiple systems of claim 1 is supplied different reagents from a fluidics manifold.

7. The system of claim 1, wherein said cuvette is removably affixed in said system by a user, and may be subsequently removed by a user.

8. The system of claim 1, wherein multiple reagents are introduced into said cuvette by the use of a fluidic manifold, and said multiple reagents may be removed from said cuvette through an exit port.

9. A system which comprises multiple systems of claim 1, wherein each of said multiple systems of claim 1 may measure fluorescence from moieties in said cuvettes.

10. A spectrometer system comprising:
a light source and a two dimensional sensor, the two dimensional sensor having a plurality of light-receiving pixels, a collimating element configured to collimate said light from said light source to provide collimated light, a cuvette arranged to contain a fluid sample, wherein said collimated light from said light source is directed through said cuvette, and a plasmonic filter set formed to contact said cuvette, said plasmonic filter set including a plurality of plasmonic filter patches formed on a substrate, each one of the plasmonic filter patches including dielectric and metallic regions to differentially transmit selected wavelengths of said collimated light received from said collimating element and directed toward corresponding one or more of pixels among the plurality of light-receiving pixels of said two dimensional sensor that are designated to said one of the plasmonic filter patches, wherein said selected wavelengths of at least some of the plurality of plasmonic filter patches differ from each other so that intensities of light received at said one or more of the designated pixels through respective ones of said at least some of the plurality of plasmonic filters patches indicate spectroscopic information of the fluid sample.

11. A spectrometer system comprising: a light source, a cuvette arranged to contain a fluid sample, wherein light from said light source is directed through said cuvette to interact with the fluid sample, and a plasmonic filter set receiving the light that has interacted with the fluid sample from the cuvette, the plasmonic filter set including a plurality of plasmonic filter patches each said-plasmonic filter including dielectric and metallic regions to differentially transmit selected wavelengths of the light received from the cuvette; wherein said selected wavelengths of at least some of the plurality of plasmonic filter patches differ from each other so that the corresponding selected wavelengths of the light received from the cuvette through said at least some of the plurality of plasmonic filters patches include spectroscopic information of the fluid sample.

* * * * *